US006448449B2

(12) United States Patent
Larrow

(10) Patent No.: US 6,448,449 B2
(45) Date of Patent: Sep. 10, 2002

(54) PROCESS FOR PREPARATION OF (R)-1- (ARYLOXY)PROPAN-2-OL

(75) Inventor: Jay Francis Larrow, Wakefield, MA (US)

(73) Assignee: Rhodia ChiRex, Inc., Boston, MA (US)

( * ) Notice: Subject to any disclaimer, the term of this patent is extended or adjusted under 35 U.S.C. 154(b) by 0 days.

(21) Appl. No.: 09/839,062

(22) Filed: Apr. 20, 2001

Related U.S. Application Data

(60) Provisional application No. 60/198,942, filed on Apr. 21, 2000.

(51) Int. Cl.$^7$ .......................... C07C 43/205; C07F 7/18
(52) U.S. Cl. ........................ 568/587; 568/588; 568/648; 568/649; 556/482
(58) Field of Search ................................ 568/587, 588, 568/648, 649; 556/482

(56) References Cited

U.S. PATENT DOCUMENTS

| 5,637,739 A | 6/1997 | Jacobsen et al. ............ 549/524 |
| 5,663,393 A | 9/1997 | Jacobsen et al. ............ 556/45 |
| 5,665,890 A | 9/1997 | Jacobsen et al. ............ 549/230 |
| 5,929,232 A | 7/1999 | Jacobsen et al. ............ 540/145 |
| 6,172,268 B1 | 1/2001 | Tohma et al. ............... 568/588 |
| 6,207,847 B1 | 3/2001 | Nugent, Jr. ................. 556/470 |

FOREIGN PATENT DOCUMENTS

| JP | 11-269131 | 10/1999 | ........... C07C/69/78 |
| JP | 11-279100 | 10/1999 | ........... C07C/43/23 |
| JP | 2000-063314 | 2/2000 | ........... C07C/43/23 |

OTHER PUBLICATIONS

Ready et al., "Asymmetric Catalytic Synthesis of α–Aryloxy Alcohols Kinetic Resolution of Terminal Epoxides via Highly Enantioselective Ring–Opening with Phenols." J. Am. Chem. Soc. 1999, 121, 6086–6087.

Annis et al., "Polymer–supported Chiral Co(Salen) Complexes: Synthetic Applications and Mechanistic Investigations in the Hydrolytic Kenetic Resolution of Terminal Epoxides." J. Am. Chem. Soc. 1999, 121, 4147–4154.

Primary Examiner—Rosalynd Keys
(74) Attorney, Agent, or Firm—Ohlandt, Greeley, Ruggiero & Perle, L.L.P.

(57) ABSTRACT

A process for the preparation of (R)-1-(2,3-difluoro-6-nitrophenoxy)-propan-2-ol, which is a useful intermediate in the synthesis of the widely used antibiotic Levofloxacin is provided. A process for the preparation of (R)-1-(2,3-difluoro-6-nitrophenoxy)-2-trimethylsiloxypropane is also described. The process includes the ring opening of (R)-propylene oxide with 2,3-difluoro-6-nitrophenyl trimethylsilyl ether in the presence of an optically active Co(salen) catalyst. The trimethylsilyl group of the reactant is transferred to the product aryloxy alcohol, which serves to protect the secondary alcohol in situ. Upon isolation, the trimethylsilyl group is removed and the resulting regioisomeric mixture purified to yield the desired (R)-1-(2,3-difluoro-6-nitrophenoxy)-propan-2-ol in high purity and yield.

32 Claims, No Drawings

PROCESS FOR PREPARATION OF (R)-1- (ARYLOXY)PROPAN-2-OL

This application claims priority from U.S. Provisional Application Ser. No. 60/198,942, filed Apr. 21, 2000.

BACKGROUND OF THE INVENTION

1. Field of the Invention

The present invention relates to a process for the preparation of an (R)-1-(aryloxy)propan-2-ol from an (R)-1-aryloxy-2-trialkylsiloxypropane with high regioselectivity and enantioselectivity. More particularly, the present invention relates to a process for the preparation of (R)-1-(2,3-difluoro-6-nitrophenoxy)-propan-2-ol from (R)-1-(2,3-difluoro-6-nitrophenoxy)-2-trimethylsiloxypropane. The (R)-1-(2,3-difluoro-6-nitrophenoxy)propan-2-ol is useful as an intermediate in the synthesis of Levofloxacin antibiotic.

2. Description of the Prior Art

U.S. Pat. No. 5,665,890 to Jacobsen et al. describes a stereoselective chemical synthesis by the reaction of a nucleophile and a chiral or prochiral cyclic substrate, such as an epoxide, in the presence of a non-racemic chiral catalyst.

U.S. Pat. No. 5,929,232, also to Jacobsen et al., describes a kinetic resolution of a cyclic substrate, such as an epoxide, in the presence of a non-racemic chiral catalyst.

U.S. Pat. Nos. 5,663,393 and 5,637,739, both to Jacobsen et al., describe catalysts that are useful in the above stereoselective chemical syntheses and kinetic resolution reactions.

The contents of U.S. Pat. Nos. 5,665,890, 5,929,232, 5,663,393 and 5,637,739, all to Jacobsen et al., are incorporated herein by reference in their entirety.

JP 10-77934 to Asahi Glass is directed to the preparation of a 1-aryloxy-2-propanol derivative.

The ring opening of epoxides with phenols has also been mentioned by Annis and Jacobsen, *J. Am. Chem. Soc.*, 121, 4147–4154 (1999) and by Ready and Jacobsen, *J. Am. Chem. Soc.*, 121, 6086–6087 (1999).

None of the above references disclose the preparation of (R)-1-(aryloxy)-2-trialkylsiloxypropane, such as, (R)-1-(2,3-difluoro-6-nitrophenoxy)-2-trimethylsiloxypropane, and its subsequent conversion to the corresponding (R)-1-(aryloxy)propan-2-ol, such as the (R)-1-(2,3-difluoro-6-nitrophenoxy)propan-2-ol, which is useful as an intermediate in the synthesis of Levofloxacin.

Accordingly, the present invention provides processes for the preparation of (R)-1-(2,3-difluoro-6-nitrophenoxy) propan-2-ol, which is a useful intermediate in the synthesis of the widely used antibiotic Levofloxacin.

SUMMARY OF THE INVENTION

The present invention includes a process for the preparation of an (R)-1-(aryloxy)propan-2-ol with high regioselectivity and enantioselectivity. The process comprises:

contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxypropane;

contacting said regioisomeric mixture of said (R)-1-aryloxy-2-trialkylsiloxypropane and said (S)-2-(aryloxy)-1-trialkylsiloxypropane and an alcohol in the presence of an acid at a temperature and for a length of time sufficient to produce a regioisomeric mixture of (R)-1-(aryloxy)propan-2-ol and (S)-2-(aryloxy) propane-1-ol;

contacting said regioisomeric mixture of (R)-1-(aryloxy) propan-2-ol and (S)-2-(aryloxy)propane-1-ol and a triarylmethyl halide in the presence of a base at a temperature and for a length of time sufficient to produce a crude mixture of (R)-1-(aryloxy)propan-2-ol and (S)-2-(aryloxy)-1-triarylmethyloxypropane; and distilling said crude mixture of (R)-1-(aryloxy)propan-2-ol and (S)-2-(aryloxy)-1-triarylmethyloxypropane to isolate said (R)-1-(aryloxy)propan-2-ol from said crude mixture.

The present invention further includes a process for the preparation of an (R)-1-(aryloxy)propan-2-ol with high regioselectivity and enantioselectivity, said process comprising the steps of:

contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxypropane;

contacting said regioisomeric mixture of said (R)-1-aryloxy-2-trialkylsiloxypropane and said (S)-2-(aryloxy)-1-trialkylsiloxypropane and an alcohol in the presence of an acid at a temperature and for a length of time sufficient to produce a regioisomeric mixture of (R)-1-(aryloxy)propan-2-ol and (S)-2-(aryloxy) propane-1-ol;

contacting said regioisomeric mixture of (R)-1-(aryloxy) propan-2-ol and (S)-2-(aryloxy)propane-1-ol and a sulfonating agent selected from the group consisting of: trifluoromethanesulfonyl halide, trifluoromethanesulfonic anhydride and a mixture thereof, in the presence of a base at a temperature and for a length of time sufficient to produce a crude mixture of (R)-1-(aryloxy) propan-2-ol and an (S)-2-(aryloxy)-1-trifluoromethansulfonyloxypropane; and distilling said crude mixture of (R)-1-(aryloxy)propan-2-ol and (S)-2-(aryloxy)-1-trifluoromethansulfonyloxypropane to isolate said (R)-1-(aryloxy)propan-2-ol from said crude mixture.

The present invention also includes a process for the preparation of an (R)-1-aryloxy-2-trialkylsiloxypropane with high regioselectivity and enantioselectivity. The process comprises: contacting an aryl trialkysilyl ether and (R)-propylene oxide in the presence of a catalyst selected from the group consisting of: a racemic and non-racemic catalyst, to produce a regioisomeric mixture of (R)-1-(aryloxy)-2-trialkylsiloxypropane and (S)-2-(aryloxy)-1-trialkylsiloxypropane.

The present invention also includes a regioisomeric mixture which is prepared by a process, which comprises: contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxy-propane.

The present invention further includes a kinetic resolution process for the preparation of an (R)-1-aryloxy-2-trialkylsiloxypropane with high regioselectivity and enantioselectivity. This process comprises the step of: contacting an aryl trialkysilyl ether and racemic propylene oxide in the presence of a non-racemic catalyst to produce a regioisomeric mixture of (R)-1-(aryloxy)-2-trialkylsiloxy-propane and (S)-2-(aryloxy)-1-trialkylsiloxypropane.

The present invention still further includes a regioisomeric mixture prepared by a kinetic resolution process comprising the step of: contacting an aryl trialkysilyl ether and racemic propylene oxide in the presence of a non-racemic catalyst to produce a regioisomeric mixture of (R)-1-(aryloxy)-2-trialkylsiloxypropane and (S)-2-(aryloxy)-1-trialkylsiloxy-propane.

Protection of the aromatic hydroxy compound reactant and the intermediate alcohol derivatives with a trialkylsilyl group prevents side reactions, such as, the "Smiles Rearrangement," which could lead to equilibration of the regioisomeric products thereby causing erosion of the enantiomeric excess as well as loss of yield of the desired regioisomer.

DETAILED DESCRIPTION

The Levofloxacin intermediate is an optically active compound having an asymmetric carbon C* at C-2. This intermediate can be prepared from the reaction of a substituted phenol (ArOH) with propylene oxide in the presence of a metal complex catalyst, under conditions that produce a product with an enantiomeric excess of the desired enantiomer, as shown below:

The antibiotic compound Levofloxacin possesses one center of asymmetry. Currently, this center is installed by the incorporation of (R)-propylene glycol through a circuitous, multi-step route involving several protection/deprotection steps of the 1,2-diol hydroxyls. Regioselective alkylation of the free primary alcohol with 2,3,4-trifluoronitrobenzene followed by a final deprotection step leads to (R)-1-(2,3-difluoro-6-nitrophenoxy)propan-2-ol, which is then converted to Levofloxacin by conventional means.

A more straightforward route to the desired intermediate is the direct ring opening of (R)-propylene oxide with 2,3-difluoro-6-nitrophenol. Ring openings of this type have been demonstrated to be catalyzed by chiral Co(salen) complexes. Among the problems associated with this route include the fact that the Co(salen) catalyst does not open the epoxide with 100% regioselectivity, leading to two possible regioisomeric products that are difficult to separate.

The present process is based on the ring opening of (R)-propylene oxide with an aryl trialkysilyl ether, such as, 2,3-difluoro-6-nitrophenyl trimethylsilyl ether, in the presence of a catalyst. The trimethylsilyl group of the reactant is transferred to the product aryloxy alcohol, thus in situ protecting the alcohol groups thereby preventing interconversion of regioisomers via the "Smiles Rearrangement". Upon isolation of the regioisomeric mixture of the silylated (R)-1-(aryloxy)-2-trialkylsiloxypropane and (S)-2-(aryloxy)-1-trialkylsiloxypropane, the trimethylsilyl group can be removed to yield a regioisomeric mixture of (R)-1-(aryloxy)propan-2-ol and (S)-2-(aryloxy)propane-1-ol, which can be further purified to produce (R)-1-(aryloxy)propan-2-ol in high purity and high overall yield. Thus, the desired (R)-1-(2,3-difluoro-6-nitrophenoxy)propan-2-ol, which is useful as an intermediate in the synthesis of Levofloxacin, can be easily prepared by the process according to the present invention.

The aryl trialkysilyl ether can be prepared by contacting an aromatic hydroxy compound and a trialkysilyl derivative, such as, trialkylsilyl halide, trialkylsilyl azide, trialkylsilyl amide, trialkylsilyl carboxylate and trialkylsilyl sulfonate. The contacting step is carried out in the presence of a catalyst, such as, an acid or a base catalyst, at a temperature and for a length of time sufficient to produce the aryl trialkysilyl ether reactant.

Preferably, the aryl group in the aryl group in the aryl trialkysilyl ether is 2,3-difluoro-6-nitrophenyl group. Therefore, the aryl trialkysilyl ether can be prepared from 2,3-difluoro-6-nitrophenol and a suitable silylating agent.

In one embodiment of the process of the present invention an aryl trialkysilyl ether and (R)-propylene oxide are contacted in the presence of a catalyst to produce a regioisomeric mixture of (R)-1-(aryloxy)-2-trialkylsiloxypropane and (S)-2-(aryloxy)-1-trialkylsiloxypropane.

Preferably, the ratio of the (R)-1-(aryloxy)-2-trialkylsiloxypropane to (S)-2-(aryloxy)-1-trialkylsiloxypropane in the regioisomeric mixture of (R)-1-(aryloxy)-2-trialkylsiloxypropane and (S)-2-(aryloxy)-1-trialkylsiloxypropane is at least 25:1, more preferably, the ratio is at least 30:1, and most preferably, the ratio is at least 49:1.

The above mixture and an alcohol, such as, methanol, ethanol, propanol or butanol, are then contacted in the presence of an acid, such as, hydrogen halide, preferably hydrogen chloride. Typically, the contacting step is carried out at room temperature for about 10 minutes to about 2 hours to remove the silyl protecting groups and to produce a regioisomeric mixture of (R)-1-(aryloxy)propan-2-ol and (S)-2-(aryloxy)propane-1-ol.

This regioisomeric mixture and a triarylmethyl halide, such as, triphenylmethyl chloride or triphenylmethyl bromide, are then contacted in the presence of a base, such as, pyridine, preferably at room temperature. Preferably, the reaction is monitored by gas chromatography until a crude mixture of (R)-1-(aryloxy)propan-2-ol and (S)-2-(aryloxy)-1-triphenylmethyloxypropane having an (R)-1-(aryloxy)propan-2-ol to (S)-2-(aryloxy)-1-triphenylmethyloxypropane ratio of >100:<1 was produced. Thereafter, a simple distillation of this crude mixture of (R)-1-(aryloxy)propan-2-ol and (S)-2-(aryloxy)-1-triphenylmethyloxypropane afforded the desired (R)-1-(aryloxy)propan-2-ol isolated product, i.e., (R)-1-(2,3-difluoro-6-nitrophenoxy)propan-2-ol, in high yield and purity.

Preferably, the ratio of the (R)-1-(aryloxy)-propan-2-ol to unreacted (S)-2-(aryloxy)propane-1-ol in the crude mixture of (R)-1-(aryloxy)propan-2-ol and (S)-2-(aryloxy)-1-triphenylmethyloxy-propane is at least 100:1 and, preferably, the ratio of (R)-1-(aryloxy)propan-2-ol to (S)-2-(aryloxy)propane-1-ol in the distilled (R)-1-(aryloxy)propan-2-ol is also at least 100:1.

In another embodiment of the process of the present invention, a regioisomeric mixture of (R)-1-(aryloxy)propan-2-ol and (S)-2-(aryloxy)propane-1-ol is prepared as before, however, this regioisomeric mixture and a sulfonating agent, instead of the triarylmethyl halide, are then contacted. As before, the contacting step is carried out in the presence of a base, such as, pyridine, and preferably, at room temperature. As before, the reaction is monitored by gas chromatography until a crude mixture of (R)-1-(aryloxy)propan-2-ol and an (S)-2-(aryloxy)-1-trifluoromethansulfonyloxypropane in a ratio of >100:<1 is produced. Thereafter, as before, a simple distillation of this crude mixture of (R)-1-(aryloxy)propan-2-ol and (S)-2-(aryloxy)-1-trifluoromethansulfonyloxypropane afforded the desired (R)-1-(aryloxy)propan-2-ol isolated product, i.e., (R)-1-(2,3-difluoro-6-nitrophenoxy)propan-2-ol, in high yield and purity.

The preferred sulfonating agents include trifluoromethanesulfonic anhydride and trifluoromethanesulfonyl halides, such as, trifluoromethanesulfonyl fluoride and trifluoromethanesulfonyl chloride, and any combinations thereof.

The reaction temperature of any of the above process steps can range from −80 to 100° C. Preferably, the reaction temperature is from about −10 to about 30° C., more preferably, the reaction temperature is about room temperature.

Trifluoromethanesulfonic anhydride (triflic anhydride) can also be used as an alternative to triphenylmethyl halide (trityl halide) in the regioisomeric purity upgrade step of the process.

The catalyst can be a racemic or a non-racemic catalyst, depending on the epoxide. When the epoxide is racemic, the catalyst must be non-racemic. However, when the epoxide is non-racemic, the catalyst can be either racemic or non-racemic. Preferably, when the epoxide is non-racemic, the catalyst is also non-racemic.

Preferably, the catalyst is a salt, such as, an inorganic salt, or is a chiral or achiral complex of a metal with suitable ligand. The preferred metals include: Co(II), Co(III), Mg(II), Zn(II), Al(III), Sc(III), Zr(IV), Ti(IV), Sn (II or IV), La(III), Yb(III) and Ce(III). Suitable ligands include oxygen, nitrogen, sulfur, phosphorus and carbon based monodentate, bidentate, tridentate or tetradentate ligands. Particularly preferred ligands are "salen" ligands disclosed in the previously incorporated U.S. Pat. Nos. 5,665,890, 5,929,232, 5,663,393 and 5,637,739, all to Jacobsen et al.

Preferably, the catalyst is a non-racemic catalyst, such as, (S,S)-Co(II)(salen) catalyst, (S,S)-Co(III)(aryloxy)(salen) catalyst or a mixture thereof, and the non-racemic catalysts disclosed in the previously incorporated U.S. Pat. Nos. 5,665,890, 5,929,232, 5,663,393 and 5,637,739, all to Jacobsen et al.

The above cobalt based catalysts have also been found to catalyze the equilibration of the regioisomers via a Smiles Rearrangement. Since internal opening of the epoxide inverts the chiral center, Smiles Rearrangement would lead to the formation of the enantiomer, eroding the enantiomeric excess (ee) of the title compound. Thus, an important advantage of the current process is that in situ silylation of the secondary alcohol prevents the Smiles rearrangement and subsequent loss in ee. In addition, isolation of the product by distillation is also facilitated by silylation. After desilylation and purification, the title compound, i.e., (R)-1-(aryloxy)-propan-2-ol, is obtained by a simple distillation step.

The preferred protecting group is trimethylsilyl group as shown in the Examples. However, any trialkylsilyl group can be used instead of the trimethylsilyl group, including, for example, silyl groups having one or more alkyl groups of 1 to 4 carbon atoms. Preferred trialkysilyl derivatives suitable for use as silylating agents include trialkylsilyl halide, trialkylsilyl azide, trialkylsilyl amide, trialkylsilyl carboxylate and trialkylsilyl sulfonate. Other silylation reagents will also be evident to those skilled in the art and therefore, are considered to be equivalent to those mentioned above.

Trialkylsilyl derivatives of other phenols of various substitution patterns also constitute an embodiment of this invention. Trialkylsilyl derivatives of alternative nucleophiles are also contemplated, especially the use of trialkylsilyl carboxylate esters and trialkylsilyl sulfonate esters. The use of alternative epoxides of all possible substitution patterns are also contemplated by the present process, with the chiral catalyst demonstrating measurable control over the regioselectivity of ring opening.

Racemic epoxides, specifically racemic propylene oxide, can also be used in the current process, with the chiral catalyst controlling not only regioselectivity, but also enantioselectivity in a kinetic resolution capable of producing product of high enantiomeric excess.

Ranges of catalyst equivalents are from 0.1 to 50 mol %, with 0.1 to 1 mol % representing the preferred embodiment. Epoxide equivalents can range from 1.0 to 50 equivalents, with 1 to 5 equivalents representing the preferred embodiment.

The epoxide, which is the reactant in the process of the present invention, can also be used as the solvent or can be used in combination with a co-solvent. When the epoxide serves as the solvent, it is generally used in excess. When used in combination with a co-solvent, any suitable co-solvent can be used. Preferred co-solvents include methyl tert-butyl ether (MTBE), dichloromethane, and tetrahydrofuran.

The present invention includes process for the preparation of an (R)-1-aryloxy-2-trialkylsiloxypropane with high regioselectivity and enantioselectivity. The process comprises: contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxypropane. The present invention also includes a regioisomeric mixture which is prepared by the above process, which comprises: contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxy-propane.

The present invention further includes a kinetic resolution process for the preparation of an (R)-1-aryloxy-2-trialkylsiloxypropane with high regioselectivity and enantioselectivity. This process comprises the step of: contacting an aryl trialkysilyl ether and racemic propylene oxide in the presence of a non-racemic catalyst to produce a regioisomeric mixture of (R)-1-(aryloxy)-2-trialkylsiloxy-propane and (S)-2-(aryloxy)-1-trialkylsiloxypropane. The present invention still further includes a regioisomeric mixture prepared by a kinetic resolution process comprising the step of: contacting an aryl trialkysilyl ether and racemic propylene oxide in the presence of a non-racemic catalyst to produce a regioisomeric mixture of (R)-1-(aryloxy)-2-trialkylsiloxypropane and (S)-2-(aryloxy)-1-trialkylsiloxypropane.

Alternative work-up and isolation procedures are also possible, and will be evident to those skilled in the art.

EXAMPLE

A. 2,3-difluoro-6-nitrophenyl trimethylsilyl Ether:

An ice-cold solution of 2,3-difluoro-6-nitrophenol (77.9 g, 1.0 equiv, 97% purity) and triethylamine (63.2 mL, 1.05 equiv) in diethyl ether (1 L) was treated with trimethylsilyl chloride (56 mL, 1.0 equiv) while maintaining the reaction temperature below 5° C. with vigorous stirring. After stirring for 2 h, the entire mixture was filtered through Celite and the solids were washed with additional portions of ether (3×200 mL). The combined filtrates were concentrated to a golden yellow oil, which was used directly in the ring opening reaction.

B. (R)-1-(2,3-difluoro-6-nitrophenoxy)-2-trimethylsiloxypropane (1):

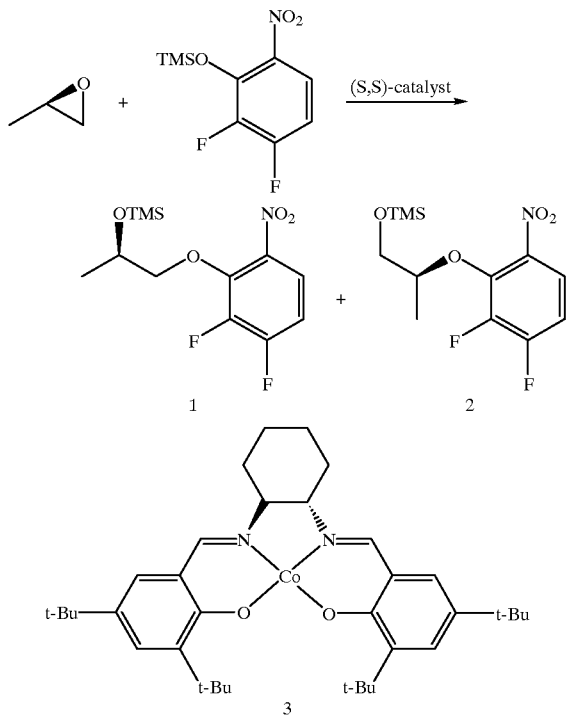

(S,S)-Co(salen) catalyst 3 (1.40 g, 2.34 mmol, 1 mol %) was stirred with 2,3-difluoro-6-nitrophenyl trimethylsilyl ether (57.7 g, 0.233 mol, 1.0 equiv) under air for 1 hour at room temperature. The mixture was then cooled to 0° C., and (R)-propylene oxide (23 mL, 0.33 mol, 1.41 equiv, from RhodiaChiRex, Inc., Boston, Mass.) was added with stirring. The flask was stoppered, and the mixture was aged for 16 hours at 0° C. The mixture was then concentrated to a reddish brown oil, which was purified by vacuum distillation through a wiped film evaporator. The product was a mixture of 1 and 2, isolated as a pale yellow liquid. Typical regioisomeric ratios of 1:2 were 25:1 to 30:1.

C. (R)-1-(2,3-difluoro-6-nitrophenoxy)propan-2-ol:

The mixture obtained from the above reaction, comprising (R)-1-(2,3-difluoro-6-nitrophenoxy)-2-trimethylsiloxypropane (1) and (S)-2-(2,3-difluoro-6-nitrophenoxy)-1-trimethylsiloxypropane (2), was dissolved in 200 mL of 10:1 CH$_2$Cl$_2$/MeOH at 0° C., and was treated with 5 mL of IM HCl in MeOH with stirring. The cooling bath was removed, and the mixture was aged for 30 minutes. The product mixture, which included (R)-1-(2,3-difluoro-6-nitrophenoxy)propan-2-ol formed by the desilylation of 1 and (S)-2-(2,3-difluoro-6-nitrophenoxy)-propane-1-ol formed by the desilylation of 2, was concentrated to a yellow oil, which was dried under high vacuum to remove the solvent. After concentration, the residue was dissolved in dichloromethane, and triphenylmethyl chloride (trityl chloride, 4 equivalents based on the undesired alcohol regioisomer (S)-2-(2,3-difluoro-6-nitrophenoxy)propane-1-ol) was added, followed by pyridine (1 equivalent based on the triphenylmethyl chloride). The mixture was stirred at ambient temperature, and the progress of the reaction was followed by gas chromatographic analysis. When the product regiomer ratio, i.e., the ratio of (R)-1-(2,3-difluoro-6-nitrophenoxy)propan-2-ol to the triphenylmeythylated (S)-2-(2,3-difluoro-6-nitrophenoxy)propane-1-ol reached >100:<1, the reaction was concentrated to dryness. The oily residue was then purified by distillation as before, using a wiped film evaporator. The compound that distilled was (R)-1-(2,3-difluoro-6-nitrophenoxy)propan-2-ol, which is the desilylated alcohol derived from 1. The triphenylmeythylated (S)-2-(2,3-difluoro-6-nitrophenoxy)propane-1-ol, i.e., (S)-2-(2,3-difluoro-6-nitrophenoxy)-1-triphenylmethyloxypropane did not distill. The overall yield for the three steps to produce (R)-1-(2,3-difluoro-6-nitrophenoxy)propan-2-ol was 90–95% based upon 2,3-difluoro-6-nitrophenol.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A process for the preparation of an (R)-1-(aryloxy)propan-2-ol with high regioselectivity and enantioselectivity, said process comprising the steps of:
    contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxypropane;
    contacting said regioisomeric mixture of said (R)-1-aryloxy-2-trialkylsiloxypropane and said (S)-2-(aryloxy)-1-trialkylsiloxypropane and an alcohol in the presence of an acid at a temperature and for a length of time sufficient to produce a regioisomeric mixture of (R)-1-(aryloxy)propan-2-ol and (S)-2-(aryloxy)propane-1-ol;
    contacting said regioisomeric mixture of (R)-1-(aryloxy)propan-2-ol and (S)-2-(aryloxy)propane-1-ol and a triarylmethyl halide in the presence of a base at a temperature and for a length of time sufficient to produce a crude mixture of (R)-1-(aryloxy)propan-2-ol and (S)-2-(aryloxy)-1-triarylmethyloxypropane; and
    distilling said crude mixture of (R)-1-(aryloxy)propan-2-ol and (S)-2-(aryloxy)-1-triarylmethyloxypropane to isolate said (R)-1-(aryloxy)propan-2-ol from said crude mixture.

2. The process of claim 1, wherein said aryl group in said aryl trialkysilyl ether is 2,3-difluoro-6-nitrophenyl.

3. The process of claim 1, wherein said alkyl group is methyl.

4. The process of claim 1, wherein said catalyst is a racemic or non-racemic catalyst.

5. The process of claim 4, wherein said catalyst is a salt or complex of a metal selected from the group consisting of: Co(II), Co(III), Mg(II), Zn(II), Al(III), Sc(III), Zr(IV), Ti(IV), Sn (II or IV), La(III), Yb(III) and Ce(III).

6. The process of claim 4, wherein said non-racemic catalyst is (S,S)-Co(II)(salen) catalyst, (S,S)-Co(III)(aryloxy)(salen) catalyst and a mixture thereof.

7. The process of claim 1, wherein the ratio of said (R)-1-(aryloxy)-2-trialkylsiloxypropane to said (S)-2-(aryloxy)-1-trialkylsiloxypropane in said regioisomeric mixture of (R)-1-(aryloxy)-2-trialkylsiloxypropane and (S)-2-(aryloxy)-1-trialkylsiloxypropane is at least 25:1.

8. The process of claim 7, wherein said (R)-1-(aryloxy)propan-2-ol is (R)-1-(2,3-difluoro-6-nitrophenoxy)propan-2-ol.

9. The process of claim 7, wherein said alcohol is methanol.

10. The process of claim 7, wherein said acid is hydrogen chloride.

11. The process of claim 1, wherein said triarylmethyl halide is triarylmethyl chloride.

12. The process of claim 11, wherein said triarylmethyl halide is triphenylmethyl chloride.

13. The process of claim 1, wherein said temperature is room temperature.

14. The process of claim 1, wherein said base is pyridine.

15. The process of claim 1, wherein the ratio of said (R)-1-(aryloxy)-propan-2-ol to said (S)-2-(aryloxy)propane-1-ol in said regioisomeric mixture of (R)-1-(aryloxy)propan-2-ol and (S)-2-(aryloxy)propane-1-ol is at least 25:1.

16. The process of claim 1, wherein the ratio of said (R)-1-(aryloxy)-propan-2-ol to unreacted (S)-2-(aryloxy)propane-1-ol in said crude mixture of (R)-1-(aryloxy)propan-2-ol and (S)-2-(aryloxy)-1-triphenylmethyloxypropane is at least 100:1.

17. The process of claim 1, wherein the ratio of said (R)-1-(aryloxy)-propan-2-ol to (S)-2-(aryloxy)propane-1-ol in said distilled (R)-1-(aryloxy)propan-2-ol is at least 100:1.

18. The process of claim 1, wherein said aryl trialkysilyl ether is prepared by a process comprising the step of:
contacting an aromatic hydroxy compound and a trialkysilyl derivative selected from the group consisting of: trialkylsilyl halide, trialkylsilyl azide, trialkylsilyl amide, trialkylsilyl carboxylate and trialkylsilyl sulfonate, in the presence of a catalyst at a temperature and for a length of time sufficient to produce said aryl trialkysilyl ether.

19. A process for the preparation of an (R)-1-aryloxy-2-trialkylsiloxypropane with high regioselectivity and enantioselectivity, said process comprising the step of:
contacting an aryl trialkysilyl ether and (R)-propylene oxide in the presence of a catalyst selected from the group consisting of: a racemic and non-racemic catalyst, to produce a regioisomeric mixture of (R)-1-(aryloxy)-2-trialkylsiloxypropane and (S)-2-(aryloxy)-1-trialkylsiloxypropane.

20. The process of claim 19, wherein the ratio of said (R)-1-(aryloxy)-2-trialkylsiloxypropane to said (S)-2-(aryloxy)-1-trialkylsiloxypropane in said regioisomeric mixture of (R)-1-(aryloxy)-2-trialkylsiloxypropane and (S)-2-(aryloxy)-1-trialkylsiloxypropane is at least 25:1.

21. The process of claim 19, wherein said ratio is at least 30:1.

22. The process of claim 19, wherein said ratio is at least 49:1.

23. A regioisomeric mixture prepared by a process comprising the step of:
contacting an aryl trialkysilyl ether and (R)-propylene oxide in the presence of a catalyst to produce a regioisomeric mixture of (R)-1-(aryloxy)-2-trialkylsiloxypropane and (S)-2-(aryloxy)-1-trialkylsiloxypropane.

24. A kinetic resolution process for the preparation of an (R)-1-aryloxy-2-trialkylsiloxypropane with high regioselectivity and enantioselectivity, comprising the step of:
contacting an aryl trialkysilyl ether and racemic propylene oxide in the presence of a non-racemic catalyst to produce a regioisomeric mixture of (R)-1-(aryloxy)-2-trialkylsiloxypropane and (S)-2-(aryloxy)-1-trialkylsiloxypropane.

25. The process of claim 24, wherein said non-racemic catalyst is a salt or complex of a metal selected from the group consisting of: Co(II), Co(III), Mg(II), Zn(II), Al(III), Sc(III), Zr(IV), Ti(IV), Sn (II or IV), La(III), Yb(III) and Ce(III).

26. The process of claim 24, wherein said non-racemic catalyst is (S,S)-Co(II)(salen) catalyst, (SS)-Co(III)(aryloxy)(salen) catalyst and a mixture thereof.

27. The process of claim 24, wherein said aryl group is 2,3-difluoro-6-nitrophenyl.

28. The process of claim 24, wherein said alkyl group is methyl.

29. The process of claim 24, wherein the ratio of said (R)-1-(aryloxy)-2-trialkylsiloxypropane to said (S)-2-(aryloxy)-1-trialkylsiloxypropane in said regioisomeric mixture of (R)-1-(aryloxy)-2-trialkylsiloxypropane and (S)-2-(aryloxy)-1-trialkylsiloxypropane is at least 25:1.

30. The process of claim 29, wherein said ratio is at least 30:1.

31. The process of claim 30, wherein said ratio is at least 49:1.

32. A regioisomeric mixture prepared by a process comprising the step of:
contacting an aryl trialkysilyl ether and racemic propylene oxide in the presence of a non-racemic catalyst to produce a regioisomeric mixture of (R)-1-(aryloxy)-2-trialkylsiloxypropane and (S)-2-(aryloxy)-1-trialkylsiloxypropane.

* * * * *